United States Patent [19]

Martens

[11] 4,053,529

[45] Oct. 11, 1977

[54] PROCESS FOR THE MANUFACTURE OF VINYLIDENE FLUORIDE

[75] Inventor: Guy Martens, Jemeppe, Belgium

[73] Assignee: Solvay & Cie, Brussels, Belgium

[21] Appl. No.: 704,798

[22] Filed: July 13, 1976

[30] Foreign Application Priority Data

July 18, 1975 Luxembourg .............................. 73023

[51] Int. Cl.$^2$ ............................................. C07C 17/34
[52] U.S. Cl. ................................................. 260/653.5
[58] Field of Search ..................................... 260/653.5

[56] References Cited

U.S. PATENT DOCUMENTS

| | | | |
|---|---|---|---|
| 2,572,913 | 10/1951 | Calfee et al. ....................... | 260/653.5 |
| 2,628,989 | 2/1953 | Miller ............................... | 260/653.5 |
| 2,899,472 | 8/1959 | Bower et al. ...................... | 260/653.5 |
| 3,246,041 | 4/1966 | Miville et al. ..................... | 260/653.5 |

*Primary Examiner*—C. Davis
*Attorney, Agent, or Firm*—Spencer & Kaye

[57] ABSTRACT

A process for the manufacture of vinylidene fluoride by pyrolysis of 1-chloro-1,1-difluoroethane at temperatures of between 500° and 610° C comprises conducting the pyrolysis in the simultaneous presence of from 0.01 to 10 mol % of carbon tetrachloride and from 0.01 to 10 mol % of chlorine, relative to the 1-chloro-1,1-difluoroethane.

5 Claims, No Drawings

PROCESS FOR THE MANUFACTURE OF VINYLIDENE FLUORIDE

BACKGROUND OF THE INVENTION

The present invention relates to a process for the manufacture of vinylidene fluoride from 1-chloro-1,1-difluoroethane. Vinylidene fluoride is a valuable monomer for the preparation of homopolymers and copolymers which exhibit high chemical resistance and heat resistance.

Vinylidene fluoride is usually prepared by thermal dehydrochlorination of 1-chloro-1,1-difluoroethane. It is known to use promoters for this reaction. For example, the pyrolysis of 1-chloro-1,1-difluoroethane can be initiated by amounts of carbon tetrachloride which are between 0.5 and 200% by weight, and preferably, between 2 and 25% by weight, of the 1-chloro-1,1-difluoroethane, as disclosed in U.S. Pat. No. 2,628,989, granted Feb. 17, 1953, in the name of Allied Chemical and Dye Corp. In U.S. Pat. No. 2,628,989, the presence of extraneously introduced elemental chlorine, even in very small amounts, is said to be detrimental to the reaction and causes the formation of undesirable byproducts.

It has also been proposed to use chlorine by itself as a promoter, in an amount of 0.5 to 4% by weight of the 1-chloro-1,1-difluoroethane, as disclosed in French Pat. No. 1,458,285, filed on July 28, 1965, in the name of Pennsalt Chemicals Corp.

SUMMARY OF THE INVENTION

In accordance with the present invention, there has now been developed a process which makes it possible to improve the degree of conversion of 1-chloro-1,1-difluoroethane and the selectivity in respect of vinylidene fluoride, as compared to these prior processes.

The present invention provides a process for the manufacture of vinylidene fluoride by pyrolysis of 1-chloro-1,1-difluoroethane at temperatures between 500° and 610° C which comprises conducting the pyrolysis in the simultaneous presence of from 0.01 to 10 mol % of carbon tetrachloride and from 0.01 to 10 mol % of chlorine, relative to the 1-chlorol-1,1-difluoroethane.

The present invention is thus characterized by the use for both promoter ingredients of very particular concentration ranges which bring about the improvement of the present invention.

DETAILED DESCRIPTION OF THE INVENTION

In the practice of the present invention, the amounts of carbon tetrachloride to be employed for the pyrolysis are between 0.01 and 10 mol % of the number of mols of 1-chloro-1,1-difluorcethane. In general, between 0.1 and 9 mol %, and preferably, between 0.2 and 8 mol %, relative to 1-chloro-1,1-difluoroethane, are used.

The amount of chlorie to be employed in the pyrolysis is generally between 0.1 and 10 mol % of the number of mols of 1-chloro-1,1-difluoroethane. In particular, between 0.1 and 8 mol %, and preferably, between 0.2 and 5 mol %, relative to 1-chloro-1,1-difluoroethane, are used. However, if the 1-chloro-1,1-difluoroethane contains 1,1-difluoroethane, the concentration of chlorine given above is increased by an amount equivalent, in mols, to the amount of 1,1-difluoroethane present in the 1-chloro-1,1-difluoroethane. Thus, if the mixture based on 1-chloro-1,1-difluoroethane contains 30% by weight of 1,1-difluoroethane, in general, from 32.5 to 40% by weight of chlorine, relative to the weight of the mixture, can, for example, be used. To further illustrate this point, assuming a 100 gram starting mixture containing 30 grams of 1,1-difluoroethane and 70 grams of 1-chloro-1,1-difluoroethane, there would be present 0.455 mole of 1,1-difluoroethane and 0.70 mole of 1-chloro-1,1-difluoroethane, which gives a potential of a total of 1.155 mols of 1-chloro-1,1-difluoroethane, assuming that all of the 1,1-difluoroethane would be converted to 1-chloro-1,1-difluoroethane during the process. The use of 32.5 weight-% of chlorine relative to the weight of the mixture corresponds to 0.458 mole of chlorine, or 0.455 mole of chlorine to transform the 1,1-difluoroethane into 1-chloro-1,1-difluoroethane and a remaining 0.003 mole of chlorine to initiate the pyrolysis. This 0.003 mole of chlorine corresponds to about 2.6 mol % chlorine relative to the potential number of mols of 1-chloro-1,1-difluoroethane. Similarly, the use of 40 weight-% of chlorine relative to the weight of the mixture corresponds to 0.563 mole of chlorine, or 0.455 mole of chlorine to transform the 1,1-difluoroethane and a remaining 0.108 mole of chlorine to initiate the pyrolysis. This 0.108 mole of chlorine corresponds to about 9.35 mol % chlorine relative to the potential number of mols of 1-chloro-1,1-difluoroethane. Thus, when a mixture of 1-chloro-1,1-difluoroethane and 1,1-difluoroethane is used, the above mol percentages for the amount of chlorine and carbon tetrachloride are based on the total potential amount of 1-chloro-1,1-difluoroethane that would result from the conversion of the 1,1-difluoroethane, and in addition, the amount of chlorine is increased by an amount equivalent, in mols, to the amount of 1,1-difluoroethane present in the 1-chloro-1,1-difluoroethane.

The chloro-1,1-difluoroethane used for the pyrolysis can be purified 1-chloro-1,1-difluoroethane or unpurified crude production material which may, for example, come from the chlorination of 1,1-difluoroethane or from any other known process. Thus, it is possible to use 1-chloro-1,1-difluoroethane containing varying amounts of 1,1-difluoroethane which are, in general, between 0 o 50% by weight, relative to the weight of 1-chloro-1,1-difluoroethane. The process according to the invention is particularly suitable for application to the pyrolysis of mixtures based on 1-chloro-1,1-difluoroethane containing from 1 to 30% by weight of 1,1-difluoroethane.

The pyrolysis pressures can be equal to, below or above atmospheric pressure. In general, pressures of between 0.8 and 30 kg/cm$^2$, and preferably, of between 1 and 20 kg/cm$^2$ are used.

The residence times can vary greatly and, in general, are between 0.1 and 500 seconds and, most frequently, between 0.5 and 200 seconds, but different residence times can be used, depending on the reaction temperature. The gas flow rates in the pryolysis furnace are, in general, between 0.01 and 20 m/sec.

The promoters (chlorine and carbon tetrachloride) can be introduced all at once at the entry of the pyrolysis furnace. However, it is also possible to provide for the promoter or promoters to be introduced in stages all along the reactor.

The process can be carried out continuously or discontinuously. The continuous or semi-continuous processes, however, are of markedly greater value for industrial implementation. The reactors advantageously comprise one or more tubes arranged in parallel or in series. It is preferred to use reactors of which the internal wall is produced of a corrosion-resistant material, such as platinum, nickel, nickel-based alloys (NIMONIC, INCONEL or MONEL), silver, glass, silica, graphite and the like. The use of alloys having a high iron content is preferably avoided. The reactor can be an empty tube or a tube provided with a nickel packing, for example. Most frequently, empty tubes are used.

The reactants, in general, enter the reactor in the gaseous form. The reactor can optionally be provided with a preheater, though this is not indispensable.

The temperature of the reactor and of the preheater, if present, can be achieved by any known means, such as a molten salt bath, an electric oven, a heating jacket, heating by means of combustion gases, and the like.

The pyrolysis can optionally be carried out in the presence of an inert gas, such as argon, nitrogen, carbon dioxide or hydrogen chloride.

The process which forms the subject of the present invention has proved particularly valuable because it makes it possible to obtain high yields of vinylidene fluoride and high degrees of conversion of 1-chloro-1,1-difluoroethane. Furthermore, if it is applied to the pyrolysis of mixtures based on 1-chloro-1,1-difluoroethane containing varying amounts of 1,1-difluoroethane, it has a particularly valuable additional advantage, namely, that the 1,1-difluoroethane is almost entirely converted in the pyrolysis furnace and, at the outlet of the latter, only vinylidene fluoride and unconverted 1-chloro-1,1-difluoroethane are found, which makes it possible to reduce the number of subsequent separation stages.

The examples which follow illustrate the remarkable results obtained in carrying out the process according to the invention. These examples, of course, do not imply any limitation.

EXAMPLE 1

Experiments 1R, 2R and 3R below were carried out by way of comparison in order to demonstrate the relative efficiencies of chlorine and of carbon tetrachloride, used by themselves, as promoters of the pyrolysis of 1-chloro-1,1-difluoroethane.

Experiments 4, 5, 6 and 7 were carried out in accordance with the invention.

Experiments 5, 6 and 7 were carried out by way of comparison with contents of chlorine and/or carbon tetrachloride below or above the preferred contents.

The reactor consists of two tube bundles in series, each bundle comprising 13 empty tubes of Inconel 600 arranged in series, 250.6 cm long and 2.16 cm in diameter.

The working conditions and the results obtained are summarized in Table I below. The contents of chlorine and of carbon tetrachloride are expressed in $^0/_{00}$ (per thousand) of the number of mols of 1-chloro-1,1-difluoroethane introduced.

The 1-chloro-1,1-difluoroethane used for the experiments contains from 1 to 2% of organic impurities.

TABLE I

| Experiment No. | 1R | 2R | 3R | 4 | 5 | 6 | 7 |
|---|---|---|---|---|---|---|---|
| Carbon tetrachloride, mol 0/00 | — | — | 31 | 66 | 45 | 94 | 1 |
| Chlorine (Cl$_2$), mol 0/00 | 55 | 23 | — | 43 | 85 | 22 | 1 |
| Temperature, °C | 554 | 555 | 558 | 560 | 554 | 552 | 552 |
| Residence time, seconds | 6.5 | 6.2 | 5.6 | 5.5 | 6.1 | 5.5 | 5.5 |
| Absolute pressure, atms | 2.5 | 2.9 | 3.5 | 2.9 | 4.9 | 4.8 | 2.6 |
| Degree of conversion of the 1-chloro-1,1-difluoroethane, % | 72 | 63 | 42 | 78 | 69 | 71 | 36 |
| Selectivity in respect of vinylidene chloride, % | 93 | 96 | 95 | 99 | 88 | 100 | 76 |

Comparison of Experiments 1R and 2R shows that the increase in the amount of chlorine added as a promoter causes a reduction in the selectivity in respect of vinylidene fluoride. Comparison of Experiments 4, and 1R, 2R and 3R shows that the simultaneous use of chlorine and of carbon tetrachloride makes it possible to improve both the degree of conversion and the selectivity, and to do so in spite of the use of an already rather high amount of chlorine. Comparison of Experiment 5 with Experiment 4 shows that too great an increase in the amount of chlorine reduces the selectivity and the degree of conversion. Equally, too great an increase in the carbon tetrachloride content reduces the degree of conversion, as shown by Experiment 6. The simultaneous use of very small amounts of chlorine and of carbon tetrachloride, as shown in Experiment 7, in contrast, does not give very good results. Comparison of Experiments 4, 5, 6 and 7 thus shows that there is an optimum range for the respective concentrations of the promoters.

EXAMPLE 2

This example shows the results obtained in the pyrolysis of mixtures based on 1-chloro-1,1-difluoroethane containing 1,1-difluoroethane.

The reaction is carried out in the same reactor as that of Example 1. Experiment 8 was carried out in accordance with the invention. Experiment 9 was carried out by way of comparison, with negligible concentrations of carbon tetrachloride.

The composition of the gases at the furnace inlet and outlet and the selectivity and degree of conversion are given in Table II.

TABLE II

| | Experiment 8 | | Experiment 9 | |
|---|---|---|---|---|
| | Furnace inlet | Furnace outlet | Furnace inlet | Furnace outlet |
| Constituents, mol 0/00 | | | | |
| Vinylidene fluoride | — | 260.3 | — | 189.5 |
| 1,1-Difluoroethane | 40.3 | 1.9 | 48.9 | 9.4 |
| 1-Chloro-1-fluoroethylene | — | 0.5 | — | 0.6 |
| 2-Chloro-1,1-difluoroethylene | — | 5.6 | — | 4.1 |
| 1-Chloro-1,1-difluoroethane | 770.0 | 290.4 | 664.1 | 377.6 |
| 2-Chloro-1,1-difluoroethane | 1.2 | 1.1 | 8.5 | 2.9 |
| Dichloro-1,1-difluoroethane | 0.1 | 1.9 | — | 2.9 |
| Carbon tetrachloride | 1.8 | 1.1 | 0.1 | 0.1 |
| Trichlorodifluoroethane | 0.1 | 1.0 | 5.5 | 5.5 |
| Various | 7.6 | 8.6 | 64.6 | 73.8 |
| Chlorine (Cl$_2$) | 53.2 | — | 75.8 | — |
| Hydrogen chloride | 125.7 | 424.5 | 132.5 | 330.5 |
| Hydrogen fluoride | — | 3.1 | — | 3.1 |
| Temperature, °C | 534 | | 524 | |
| Absolute pressure, atms | 4.1 | | 3.0 | |
| Residence time, secs | 7 | | 6.4 | |

TABLE II-continued

|  | Experiment 8 | | Experiment 9 | |
| --- | --- | --- | --- | --- |
|  | Furnace inlet | Furnace outlet | Furnace inlet | Furnace outlet |
| Degree of conversion of the mixture of 1,1-difluoroethane + 1-chloro-1,1-difluoroethane, % |  | 48 |  | 40 |
| Selectivity in respect of vinylidene fluoride relative to the mixture of 1,1-difluoroethane + 1-chloro-1,1-difluoroethane, % |  | 95 |  | 72 |

Examination of the above Table II shows that, if 1-chloro-1,1-difluoroethane containing a little 1,1-difluoroethane is used, the latter is practically completely converted without detracting from the selectivity of the reaction. If the same reaction is carried out virtually in the absence of carbon tetrachloride, a much worse selectivity is obtained as shown by Experiment 9.

It will be understood that the above description of the present invention is susceptible to various modifications, changes and adaptations, and the same are intended to be comprehended within the meaning and range of equivalents of the appended claims.

What is claimed is:

1. Process for the manufacture of vinylidene fluoride by pyrolysis of 1-chloro-1,1-difluoroethane at temperatures of between 500° and 610° C, comprising conducting the pyrolysis in the simultaneous presence of from 0.01 to 10 mol % of carbon tetrachloride and from 0.01 to 10 mol % of chlorine, relative to the 1-chloro-1,1-difluoroethane.

2. The process according to claim 1, wherein from 0.2 to 8 mol % of carbon tetrachloride and from 0.2 to 5 mol % of chlorine, relative to the 1-chloro-1,1-difluoroethane, are used.

3. The process according to claim 1, wherein the 1-chloro-1,1-difluoroethane that is pyrolyzed contains from 0 to 50% by weight of 1,1-difluoroethane, relative to the weight of 1-chloro-1,1-difluoroethane, and the said mol percentages are based on the total potential amount of 1-chloro-1,1-difluoroethane that would result from the total conversion of 1,1-difluoroethane to 1-chloro-1,1-difluoroethane, and wherein the amount of chlorine is increased by an amount equivalent, in mols, to the amount of 1,1-difluoroethane present in the 1-chloro-1,1difluoroethane.

4. The process according to claim 3, wherein the said mol percentages based on the total potential amount of 1-chloro-1,1-difluoroethane are from 0.2 to 8 mol % of carbon tetrachloride and from 0.2 to 5 mol % of chlorine.

5. The process according to claim 1, wherein the 1-chloro-1,1-difluoroethane that is pyrolyzed contains from 1 to 30% by weight of 1,1-difluoroethane, relative to the weight of 1chloro-1,1-difluoroethane.

* * * * *